(12) United States Patent
Chang et al.

(10) Patent No.: US 12,281,054 B2
(45) Date of Patent: Apr. 22, 2025

(54) PROCESS FOR THE PRODUCTION OF RENEWABLE DISTILLATE-RANGE HYDROCARBONS

(71) Applicant: Chevron U.S.A. Inc., San Ramon, CA (US)

(72) Inventors: Bong Kyu Chang, Novato, CA (US); Hye-Kyung Cho Timken, Albany, CA (US); Michelle K. Young, Marvel, TX (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 18/738,697

(22) Filed: Jun. 10, 2024

(65) Prior Publication Data
US 2024/0327314 A1  Oct. 3, 2024

Related U.S. Application Data

(62) Division of application No. 18/116,747, filed on Mar. 2, 2023, now Pat. No. 12,043,589, which is a division of application No. 17/750,663, filed on May 23, 2022, now Pat. No. 11,639,320.

(51) Int. Cl.
C07C 2/22  (2006.01)
C10G 50/02  (2006.01)

(52) U.S. Cl.
CPC ............ *C07C 2/22* (2013.01); *C10G 50/02* (2013.01); *C07C 2527/06* (2013.01); *C07C 2527/122* (2013.01); *C07C 2527/125* (2013.01); *C07C 2527/128* (2013.01)

(58) Field of Classification Search
CPC ............... C07C 2/22; C07C 2527/125; C07C 2527/122; C07C 2527/128; C10G 50/02
See application file for complete search history.

(56) References Cited

U.S. PATENT DOCUMENTS

| | | |
|---|---|---|
| 8,586,812 B2 | 11/2013 | Timken et al. |
| 2012/0238787 A1 | 9/2012 | Gruber et al. |
| 2014/0051897 A1 | 2/2014 | Peters et al. |
| 2016/0289574 A1 | 10/2016 | Timken et al. |
| 2016/0312133 A1 | 10/2016 | Fichtl et al. |
| 2019/0100476 A1 | 4/2019 | Yang |

OTHER PUBLICATIONS

N.M. Eagan, M.D. Kumbhalkar, U.S. Buchanan, J.A. Dumesic and G.W Huber "Chemistries and processes for the conversion of ethanol into middle-distillate fuels" Nat. Rev. Chem. 2019, 3, 223-249.

Primary Examiner — Thuan D Dang
(74) Attorney, Agent, or Firm — Merchant & Gould PC

(57) ABSTRACT

A process for producing renewable distillate-range hydrocarbons is provided. The process includes dehydrating a renewable C2-C6 alcohol feedstock to produce an olefin, oligomerizing the olefin the presence of a halometallate ionic liquid catalyst to produce an oligomer product and hydrogenating the oligomer product or fractions thereof to produce saturated distillate-range hydrocarbons.

6 Claims, 4 Drawing Sheets

PROCESS FOR THE PRODUCTION OF RENEWABLE DISTILLATE-RANGE HYDROCARBONS

RELATED APPLICATIONS

This application is a divisional of U.S. patent application Ser. No. 18/116,747, filed Mar. 2, 2023, which is a divisional of U.S. patent application Ser. No. 17/750,663, filed May 23, 2022 (U.S. Pat. No. 11,639,320 issued May 2, 2023), the contents of which are hereby incorporated by reference in their entirety.

FIELD

Processes are disclosed for obtaining fuels and fuel blends for production of alternate fuels including jet fuels and diesel fuels. Fuel-range hydrocarbons may be derived from renewable light olefin-containing feedstocks and renewable alcohol-containing feedstocks.

BACKGROUND

As the demand for diesel and jet boiling range fuel increases worldwide, there is increasing interest in feedstock sources other than petroleum crude oil.

Light olefins (C2-C6 olefins) are important intermediates in the petrochemical industry, and they are often produced commercially through steam or catalytic cracking of petroleum-derived hydrocarbons. A variety of processes and catalysts have been developed for upgrading light olefins to higher boiling, high-quality distillate-range fuels, such as jet and diesel fuels.

The production of distillate-range fuels from biomass-derived alcohols has recently received attention due to the projected increase in the demand of these fuels and the commercialization of alcohol production.

Therefore, technologies for the conversion of alcohols into diesel and jet fuel blendstocks which can take advantage of the existing infrastructure are desirable. The most common technologies involve acid-catalyzed alcohol dehydration to olefins followed by olefin oligomerization with solid acids or transition metals. Conventional acid catalysts cannot oligomerize ethylene to make distillate-range hydrocarbons with acceptable conversion and selectivity. Therefore, there is a need for improved technologies for the conversion of alcohols to distillate-range hydrocarbons.

SUMMARY

In a first aspect, there is provided a process for producing distillate-range hydrocarbons, the process comprising: (a) dehydrating a renewable alcohol having from 2 to 6 carbon atoms to form a C2-C6 olefin stream and a water stream wherein a conversion of the renewable alcohol is 95% or more; (b) separating the C2-C6 olefin stream from the water stream, wherein an amount of oxygenates in the olefin stream is less than 1 wt. %; (c) contacting the C2-C6 olefin stream with a halometallate ionic liquid catalyst, the halometallate ionic liquid catalyst comprising an organic cation and a halometallate anion, in an oligomerization reactor under oligomerization conditions to form a mixture comprising the halometallate ionic liquid catalyst and an oligomer product, wherein at least 50 wt. % of the oligomer product has boiling point distribution of from 150° C. to 400° C.; and (d) separating the oligomer product from the halometallate ionic liquid catalyst.

In a second aspect, there is provided a renewable diesel fuel produced according to the process disclosed herein which meets or exceeds the requirements of ASTM D975-21.

In a third aspect, there is provided a renewable jet fuel produced according to the process disclosed herein which meets or exceeds the requirements of ASTM D1655-21c.

In a fourth aspect, there is provided an olefin oligomer composition comprising (a) 95 wt. % or more mono-olefins having an average carbon number from 20 to 30, (b) a carbon number ranging from 9 to 50, and (c) a branching index of from 50 to 70; wherein greater than 80 wt. % of the composition has a boiling point distribution from 250° F. to 700° F. (121° C. to 371° C.).

DETAILED DESCRIPTION

Glossary

Figure 1:
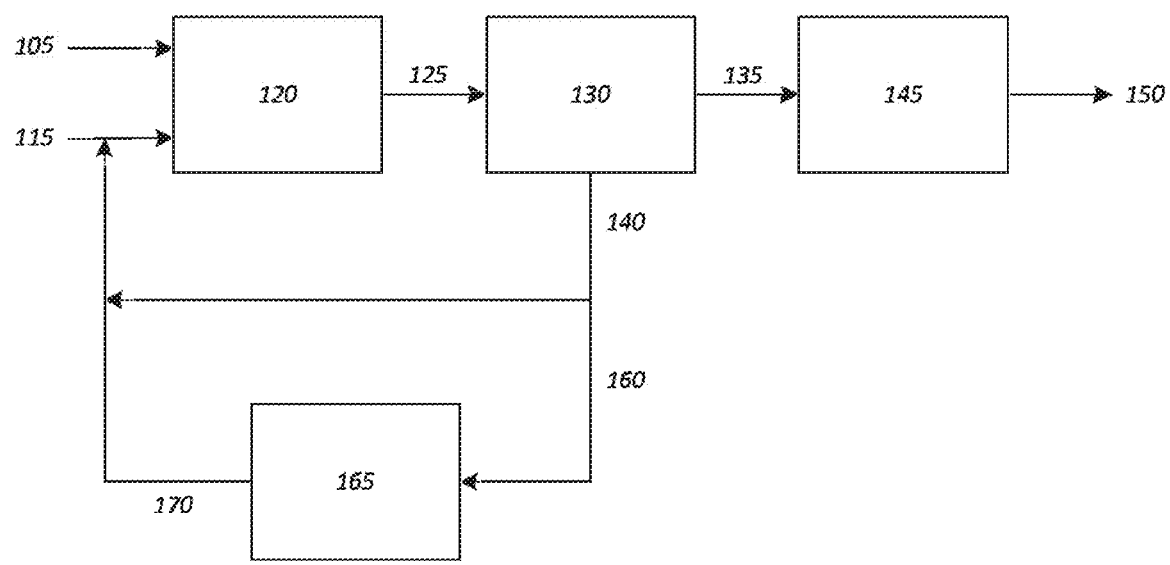
FIG. 1 shows a process flow diagram illustrating an exemplary oligomerization process.

The term "renewable" refers to a material that can be produced or is derivable from a natural source which is periodically (e.g., annually or perennially) replenished through the actions of plants of terrestrial, aquatic or oceanic ecosystems (e.g., agricultural crops, edible and non-edible grasses, forest products, seaweed, or algae), or microorganisms (e.g., bacteria, fungi, or yeast). Fossil-based resources, such a crude oil (petroleum), natural gas, and coal, are not considered renewable resources. For clarity and for the purposes of the present disclosure, the terms "renewable", "bio-based", "non-petroleum", and "non-fossil-derived" may be used interchangeably.

The term "jet-range hydrocarbons" refers to are defined as any hydrocarbon or hydrocarbon mixture that distills in the range from about 120° C. to about 300° C. and typically includes hydrocarbons with a carbon number between about C8 and about C16.

The term "jet fuel" refers to a mixture typically comprising primarily hydrocarbon compounds that can be used to operate a jet engine. Jet fuel can also include optional non-hydrocarbon additives. In practical terms, the mixture of hydrocarbons and optional additives called jet fuel must at least meet key ASTM specifications for jet fuel listed in ASTM specification D1655. Typical petroleum-based jet fuels consist primarily of straight chain alkanes, with C12 alkanes as the major component, and lesser amounts of aromatics and smaller and larger alkanes.

The term "diesel-range hydrocarbons" refers to any hydrocarbon or hydrocarbon mixture that distills in the range of about 160° C. to about 390° C., typically with a carbon number between about C11 and about C23.

The term "diesel fuel" refers to a mixture typically comprising primarily hydrocarbon compounds that can be used to operate a diesel engine. In practical terms, the mixture of hydrocarbons called diesel fuel must meet key ASTM specifications for diesel fuel listed in ASTM specification D975. Typical petroleum-based diesel fuels consist of primarily linear alkanes with C14-C15 alkanes as the major component, and lesser amounts of smaller and larger alkanes.

The term "distillate" comprises a mixture of diesel and jet-range hydrocarbons and can include hydrocarbons having a boiling point temperature in the range of about 120° C. to about 400° C. at atmospheric pressure.

The term "olefin" refers to non-aromatic hydrocarbons that have at least one carbon-carbon double bond.

The term "tri-substituted olefin" as used herein refers to a compound having at least one carbon-carbon double bond where there are two substituents attached to one carbon of the olefin carbon-carbon double bond and one and only one substituent attached to the other carbon atom of the olefin carbon-carbon double bond.

The term "substituted" when used to describe a compound or group, for example, when referring to a substituted analog of a particular compound or group, is intended to describe any non-hydrogen moiety that formally replaces a hydrogen in that group.

The term "oligomer" refers to compositions having 2-75 mer units and the term "polymer" refers to compositions having 76 or more mer units. A "mer" is defined as a unit of an oligomer or polymer that originally corresponded to the olefin(s) used in the oligomerization or polymerization reaction. For example, the mer of polyethylene would be ethylene.

The term "Cn hydrocarbons" or "Cn", is used herein having its well-known meaning, that is, wherein "n" is an integer value, and means hydrocarbons having that value of carbon atoms. The term "Cn+ hydrocarbons" or "Cn+" refers to hydrocarbons having that value or more carbon atoms. The term "Cn− hydrocarbons" or "Cn−" refers to hydrocarbons having that value or less carbon atoms.

The term "selectivity" refers to the amount of production of a particular product (or products) as a percent of all products resulting from a reaction. For example, if 100 grams of products are produced in a reaction and 80 grams of olefins are found in these products, the selectivity to olefins amongst all products is 80/100=80%. Selectivity can be calculated on a mass basis, as in the aforementioned example, or it can be calculated on a molar basis, where the selectivity is calculated by dividing the moles a particular product by the moles of all products. Unless specified otherwise, selectivity is on a mass basis.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

Dehydration

In the dehydration step, a renewable alcohol having from 2 to 6 carbon atoms is converted to its corresponding olefin (i.e., an olefin having the same number of carbon atoms as the alcohol precursor) by reacting the alcohol over a dehydration catalyst under appropriate conditions.

The alcohol starting material considered herein is generally of the formula R—OH, where R is a straight-chain or branched alkyl group having at least two carbon atoms and up to six carbon atoms. In some embodiments, the alcohol contains two to four (2-4) carbon atoms. The alcohol is typically a primary or secondary alcohol. Some examples of suitable alcohols include ethanol, 1-propanol, 2-propanol, 1-butanol, 2-butanol, isobutanol (2-methyl-1-propanol), 1-pentanol, isopentanol (3-methyl-1-butanol), 1-hexanol, and isohexanol (4-methyl-1-pentanol). The alcohol may be a single alcohol or a mixture (e.g., two, three, or more) of alcohols.

The alcohol can be in any concentration, including pure (dry) alcohol (i.e., at or about 100%) or in aqueous solution. In some aspects, the alcohol is a bio-alcohol, i.e., an alcohol that can be produced by a fermentation process. Most notable examples of bio-alcohols considered herein include ethanol, 1-butanol, and isobutanol, as commonly found in fermentation streams. In particular aspects, the alcohol is an aqueous solution of alcohol (i.e., the alcohol is a component of an aqueous solution), such as found in fermentation streams. In fermentation streams, the alcohol is typically present in a concentration of no more than about 20 wt. %, or 15 wt. %, or 10 wt. %, or 5 wt. %. In some embodiments, a fermentation stream or other alcoholic aqueous solution is directly contacted with the dehydration catalyst (typically, after filtration to remove solids) to effect the conversion of the alcohol in the fermentation stream. In other aspects, the fermentation stream or other alcoholic aqueous solution is concentrated in alcohol (for example, of at least or up to 30 wt. %, or 35 wt. %, or 40 wt. %, or 45 wt. %, or 50 wt. %) by any means known in the art (e.g., distillation, absorption, pervaporation) before contacting the fermentation stream with the dehydration catalyst. In yet other aspects, alcohol in the fermentation stream or other alcoholic aqueous solution is selectively removed from the alcoholic aqueous solution, such as by distillation, to produce a substantially pure form of alcohol as the feedstock (e.g., a concentration of at least 90 wt. % or 95 wt. % of alcohol). In still other aspects, the alcohol is completely dewatered into 100% alcohol before contacting with the dehydration catalyst.

In some aspects, the alcohol can comprise at least at least 35 wt. % (e.g., at least 50 wt. %, or at least 75 wt. %, or at least 90 vol. %, or at least 95 vol. %) of ethanol; alternatively, 1-propanol; alternatively, 2-propanol; alternatively, 1-butanol; or alternatively, isobutanol.

The alcohol may optionally undergo pretreatment prior to dehydration. Pretreatment may be implemented to remove any impurities (e.g., nitrogen-containing compounds and sulfur-containing compounds) contained in the alcohol feedstock so as to limit deactivation of the downstream dehydration catalyst. Oxygen-based compounds present in the feedstock are not substantially removed. Pretreatment may be implemented by means known in the art, such the use of at least one resin (e.g., an acidic resin) or the adsorption of the impurities onto solids preferably at a temperature of from 20° C. to 60° C. In the case where the pretreatment is implemented by the adsorption of the impurities on solids, the solids may be selected from molecular sieves, activated carbon, and alumina.

Any suitable catalysts and operating conditions may be used for dehydration.

Suitable dehydration catalysts include solid acid catalysts. Representative solid acid catalysts include inorganic oxides (e.g., g-$Al_2O_3$, $MgO/SiO_2$), molecular sieves (e.g., ZSM-5), and heteropolyacids (e.g., tungstophosphoric acid, molybdophosphoric acid).

The dehydration reactor may be operated at a temperature of from 200° C. to 500° C. (e.g., 300° C. to 450° C.).

The pressure may be in a range of from about 100 kPa to 3447 kPa (e.g., 200 kPa to 2000 kPa, or 200 kPa to 1000 kPa).

Alcohol feed may be introduced into the dehydration reactor at a liquid hourly space velocity (LHSV) ranging from 0.1 to 30 $h^{-1}$ (e.g., 0.5 $h^{-1}$ to 5 $h^{-1}$). The LHSV is defined as the volume of reactant fed to a reactor per hour divided by the volume of the catalyst in the reactor.

Any suitable reactor may be used for dehydration. The dehydration reactor can be a fixed bed reactor (radial, isothermal, adiabatic, etc.), a moving bed reactor, a multi-tubular reactor or a fluidized bed reactor.

The effluent stream from the dehydration reactor comprises essentially water, olefin, unconverted alcohol (if any), and trace amounts of impurities such as CO, $CO_2$, $H_2S$, and $H_2$. Olefin may be recovered by conventional means, such as distillation.

Preferably, the dehydration process is conducted at process conditions sufficient to achieve a high alcohol conversion. In some aspects, the alcohol conversion can be 95% or higher (e.g., 96% or higher, or 97% or higher, or 98% or higher, or 99% or higher). At low conversion of alcohol, the process produces undesirable oxygenates such as ethers and isomerized alcohols. By selecting the process conditions to achieve high conversion of alcohol lowers the concentration of oxygenates and increase the olefin selectivity. The dehydration process can have a high olefin selectivity. In some aspects, the olefin selectivity can be at 90% or higher (e.g., 95% or higher, or 99% or higher).

Oligomerization

Distillate-range hydrocarbons may be produced by contacting the C2-C6 olefin stream from the dehydration step with a halometallate ionic liquid catalyst in an oligomerization reactor under oligomerization conditions in one or multiple stages.

A dehydrated olefin containing less than 1 wt. % of oxygenates and less than 100 ppm water is a desirable feed for the olefin oligomerization step using a halometallate ionic liquid catalyst. Oxygenates and water in the olefin feed may hydrolyze the halometallate ionic liquid catalyst and may cause performance and/or operational issues. If a dehydrated olefin feed contains oxygenates and moisture, then it is desirable to treat the feed with solid adsorbents to remove oxygenates and moisture.

The ionic liquid comprises an organic cation and a halometallate anion. The organic cation may be nitrogen-based cation, a phosphorus-based cation, or a combination thereof. Representative organic cations include ammonium, pyrrolidinium, pyridinium, imidazolium, and phosphonium cations.

Examples of ammonium cations include tetraalkylammonium cations, such as tri(C1-C6 alkyl)-(C2-C10 alkyl)ammonium cations. Representative ammonium cations include propyltrimethylammonium, butyltrimethylammonium, hexyltrimethylammonium, triethylmethylammonium, tetraethylammonium, butyltriethylammonium, and tetrabutylammonium.

Examples of pyrrolidinium cations include N-alkylpyrrolidinium cations, such as 1-(C2-C6 alkyl)pyrrolidinium cations, and 1,1-dialkylpyrrolidinium cations, such as 1-(C1-C3 alkyl)-1-(C2-C6 alkyl)pyrrolidinium cations. Representative pyrrolidinium cations include 1-propylpyrrolidinium, 1-butylpyrrolidinium, 1-methyl-1-propylpyrrolidinium and 1-butyl-1-methylpyrrolidinium Examples of imidazolium cations include 1,3-dialkylimidazolium cations, such as 1-(C2-C10 alkyl)-3-(C1-C3 alkyl) imidazolium cations. Representative imidazolium cations include 1-ethyl-3-methylimidazolium, 1-butyl-3-methylimidazolium, 1-hexyl-3-methylimidazolium, and 1-octyl-3-methylimidazolium.

Examples of pyridinium cations include 1-alkylpyridinium cations, such as 1-(C2-C6 alkyl)pyridinium cations, and 1-alkyl-alkylpyridinium cations, such as 1-(C2-C6 alkyl)-(C1-C3 alkyl)pyridinium cations. Representative pyridinium cations include 1-ethylpyridinium, 1-butylpyridinium, 1-propyl-4-methylpyridinium and 1-butyl-4-methylpyridinium Examples of phosphonium cations include tetraalkylphosphonium cations, such as tri(C1-C10 alkyl)-(C2-C20 alkyl) phosphonium cations. Representative phosphonium cations include triethyl-pentylphosphonium, tetrabutylphosphonium, and trihexyl(tetradecyl)phosphonium.

The anion of the ionic liquid comprises a halometallate. Halometallate anions may contain a metal selected from Al, Ga, In, Mn, Fe, Co, Ni, Cu, Zn, or combinations thereof, and a halide selected from F, Cl, Br, I, or combinations thereof. In some aspects, the anion of the ionic liquid comprises a haloaluminate. In some aspects, the anion of the ionic liquid comprises a chloroaluminate. For catalytic applications requiring Lewis acidity (such as alkylation), the ratio of moles of halide to moles of metal in the halometallate anion is less than 4. The anion may be formally an anion or it may be an anion associated with a metal halide. For instance, the anion may be $[AlCl_4]^-$ or $[Al_2Cl_7]^-$ associated with $AlCl_3$. In some aspects, the anion may be $[GaCl_4]^-$ or $[Ga_2Cl_7]^-$ or $[Ga_3Cl_{10}]^-$ associated with $GaCl_3$.

The ionic liquid catalyst can be used in combination with a co-catalyst (or catalyst promoter) to enhance the activity of the ionic liquid catalyst by boosting its overall acidity. The co-catalyst may be a Brønsted acid and/or a Brønsted acid precursor. Suitable Brønsted acids can include HCl, HBr, and HI. The co-catalyst may be generated in situ from appropriate Brønsted acid precursors. Suitable Brønsted acid precursors can include chloroalkanes such as methylene chloride, chloroform, carbon tetrachloride, tetrachloroethylene, 1-chloropropane, tetrachloropropene, 2-chloropropane, 1-chlorobutane, 2-chlorobutane, 2-chloro-2-methylpropane, 1-chloro-2-methylpropane, 1-chlorobutane, and any. The co-catalyst may be present in an amount of 0.05 mol to 1 mol of co-catalyst per mol of ionic liquid, such as 0.05 mol to 0.7 mol, or 0.05 mol to 0.5 mol, or 0.15 mol to 0.7 mol, or 0.15 mol to 0.5 mol co-catalyst per mol of ionic liquid.

The oligomerization can be carried out in any suitable reactor. Examples of reactor types can include a stirred tank reactor, a loop reactor, a tubular reactor, or any combination thereof. The oligomerization can be carried out in more than one reactor in series or in parallel and including any combination of reactor types and arrangements.

The oligomerization can be conducted in a semi-batch or continuous mode. By "continuous" is meant a process that operates (or is intended to operate) without interruption or cessation. For example, a continuous process would be one where reactants (e.g., olefin feed, the ionic liquid catalyst and optional co-catalyst) are continually introduced into one or more reactors and a product stream comprising oligomer product is continually withdrawn. By "semi-batch" is meant a system that operates (or is intended to operate) with periodic interruption. For example, a semi-batch process to produce the oligomer product would be one where the reactants are continually introduced into one or more reactors and the product stream is intermittently withdrawn.

The oligomerization can be performed at any suitable oligomerization temperature and pressure.

Oligomerization conditions may include an operating temperature in a range of from 10° C. to 200° C. (e.g., 20° C. to 150° C., or 35° C. to 130° C.).

The pressure may be in a range of from 10 psig to 1000 psig (68.9 kPa to 6.9 MPa), such as 30 psig to 725 psig (210 kPa to 5.0 MPa), or 50 psig to 600 psig (350 kPa to 4.1 MPa).

In one example, the oligomerization is carried out a temperature of from 35° C. to 130° C., and a pressure of from 30 psig to 600 psig (210 kPa to 4.1 MPa). Ethylene oligomerization requires high pressure over 300 psig due to lower reactivity and high vapor pressure while other C3-C6 olefins require much lower pressure of less than 100 psig.

The residence time of the reactants in the reaction zone can range from 1 minute to 5 hours (e.g., 5 minutes to 2.5 hours, or 10 minutes to 2 hours). In some aspects, such as continuous process embodiments, the reaction time (or residence time) can be stated as an average reaction time (or average residence time) and can range from 1 minute to 5 hours (e.g., 5 minutes to 2.5 hours, or 10 minutes to 2 hours).

The volume of ionic liquid in the oligomerization reactor may be in a range of from 0.5 vol. % to 50 vol. % of the total volume of material in the reactor (ionic liquid catalyst and hydrocarbons), or 1 vol. % to 50 vol. %, or 1 vol. % to 45 vol. %, or 1 vol. % to 40 vol. %, or 1 vol. % to 35 vol. %, or 1 vol. % to 30 vol. %, or 1 vol. % to 25 vol. %, or 1 vol. % to 20 vol. %, or 1 vol. % to 15 vol. %, or 1 vol. % to 10 vol. %, or 1 vol. % to 5 vol.

Due to the low solubility of hydrocarbons in ionic liquids, oligomerization, like most reactions in ionic liquids, is generally biphasic and takes place at the interface in the liquid state. Vigorous mixing is desirable to ensure good contact between the reactants and the catalyst.

The oligomerization may be carried out in an inert hydrocarbon diluent. An inert diluent is one that does not interfere substantially with the oligomerization process. The hydrocarbon diluent may be selected from an alkane such as an C3-C12 alkane. Specific examples of the hydrocarbon diluent may include propane, n-butane, n-hexane, and n-heptane. The amount of diluent is not particularly limited and may be conventionally selected.

At the reactor outlet, the hydrocarbon phase is separated from the ionic liquid phase by gravity settling based on density differences, or by other separation techniques known in the art. Then the hydrocarbons are separated by distillation, and any starting olefins which have not been converted may be recycled to the reactor. The catalyst is typically recycled to the reactor as well.

In a semi-batch system, the ionic liquid catalyst, optional co-catalyst, and at least a portion of the hydrocarbon diluent are introduced into the reactor with no olefin present, followed by the olefin. In a semi-batch system, the olefin is added gradually over a period of time. The catalyst is measured in the reactor with respect to the amount of total hydrocarbon added over the course of the reaction, with a catalyst to hydrocarbon weight ratio in a range of from 1:1 to 1:1000.

In a continuous system, the ionic liquid catalyst, the olefin, and optionally the co-catalyst are each added continuously. Catalyst, optional co-catalyst, and any unreacted olefin are each removed continuously from the reaction zone along with oligomer product. The catalyst, co-catalyst, and/or unreacted olefin may be recycled. The olefin may be added to one or more locations in the reaction zone.

The feed rates of the reactants and the catalyst to the reactor are adjusted to a desirable residence time of olefin feed source for optimized oligomerization product formation. The residence time typically ranges from 3 minutes to 240 minutes. Ethylene oligomerization requires a longer residence time of 30 to 240 minutes due to lower reactivity. Other C3-C6 olefins require much shorter residence time in the range of 3 to 60 minutes.

Conjunct polymer forms as a by-product of the oligomerization reaction. Conjunct polymers are typically highly conjugated, olefinic, highly cyclic hydrocarbons and have a strong affinity for the ionic liquid catalyst. The ionic liquid catalyst loses its effectiveness over time as the amount of conjunct polymer increases. Over time, the ionic liquid catalyst must then either be replaced or regenerated. Generally, only as much ionic liquid catalyst is regenerated as is necessary to maintain a desired level of catalyst activity. Generally, the oligomerization process is operated at conditions sufficient to maintain a desired level of conjunct polymer in the ionic liquid. The amount of conjunct polymer in the ionic liquid during oligomerization may be maintained at 10 wt. % or less (e.g., 9 wt. % or less, or 8 wt. % or less, or 7 wt. % or less, or 6 wt. % or less, or 5 wt. % or less, or 4 wt. % or less, or 3 wt. % or less, or 2 wt. % or less, or 1 wt. % or less). For example, the amount of conjunct polymer in the spent ionic liquid may be maintained in a range of from 0.5 wt. % to 10 wt. %, or 1 wt. % to 5 wt. %, or 2 wt. % to 4 wt. %. An amount of conjunct polymer in an ionic liquid phase can determined by conventional methods known in the art such as by infrared spectroscopy.

FIG. 1 illustrates an exemplary oligomerization process utilizing the halometallate ionic liquid catalyst. An olefin feed stream 105 and a haloaluminate ionic liquid catalyst composition stream 115, optional co-catalyst and inert hydrocarbon medium, are fed to an oligomerization zone 120. Olefin reacts in the presence of the haloaluminate ionic liquid catalyst composition at oligomerization conditions to form an oligomer product. In some aspects, the olefin feed stream, the ionic liquid catalyst, co-catalyst and inert hydrocarbon medium are introduced into the oligomerization zone 120 simultaneously. In other aspects, the inert hydrocarbon medium is initially introduced into the oligomerization zone 120, followed by ionic liquid catalyst, co-catalyst, and olefin feed stream.

The effluent 125 from the oligomerization zone 120 contains oligomer product, the halometallate ionic liquid catalyst, and possibly unreacted olefins. The effluent 125 is sent to a separation zone 130 where it is separated into a hydrocarbon stream 135 comprising the oligomer product and an ionic liquid recycle stream 140 comprising the halometallate ionic liquid catalyst. Suitable separation zones include gravity settlers, coalescers, filtration zones comprising sand or carbon, adsorption zones, scrubbing zones, or any combination thereof.

The hydrocarbon stream 135 is sent to a hydrocarbon separation zone 145 where oligomer product is separated to obtain a desired fraction. The oligomer product stream 150 can be recovered and further treated as needed. Suitable hydrocarbon separation zones include distillation or vaporization units.

The ionic liquid recycle stream 140 can be recycled to the oligomerization zone 120, if desired. In some aspects, at least a portion 160 of the ionic liquid recycle stream 140 can be sent to a regeneration zone 165 to regenerate the halometallate ionic liquid catalyst. The regenerated ionic liquid recycle stream 170 can be recycled to the oligomerization zone 120.

The oligomerization can be operated to obtain any desired olefin conversion to the olefin oligomer product. Generally, the olefin conversion can be any which provides a desired) productivity, product purity, and/or process economics, among other factors. In some embodiments, the minimum olefin conversion can be at least 20 wt. % (e.g., at least 30 wt. %, or at least 40 wt. %, or at least 45 wt. %; or at least 50 wt. %; or at least 55 wt. %; or at least 60 wt. %). In aspects where the olefin oligomerization is practiced in a continuous reactor, the olefin conversion (any described herein) can be a single pass olefin conversion.

It is preferred to achieve high olefin conversion, then this will minimize the amount of unreacted olefin to be recycled. However, simply extending the reaction time to increase the conversion is not preferred since extended oligomerization may make the molecular weight of the oligomer very high causing the material to boil beyond the distillate product range. Thus, it is desirable to optimize the oligomerization process conditions to maximize the distillate product yields while pursuing a high conversion of olefins. In this invention, we discovered the amount of ionic liquid catalyst, reactor temperature, and the amount of co-catalyst are the critical variables that need to be optimized for each olefin feed source to maximize the distillate yield.

Oligomer Product

The oligomer product may comprise dimers, trimers, tetramers, pentamers, and higher oligomers of the olefin feedstock components. The olefin feedstock components that compose the oligomers may be the same or different. For example, a dimer of C2 and C4 components results in a C6 oligomer. In another example, a dimer of C4 components results in a C8 oligomer.

Oligomer products obtained from the oligomerization may include linear and branched olefin hydrocarbons with a carbon number range from C4 to C60 (e.g., C10 to C60, or C10 to C50, or C10 to 40, or C10 to C30).

In some aspects, the oligomer product may comprise at 30 wt. % (e.g., at least 40 wt. %, or at least 50 wt. %) C20+ olefins. For example, the oligomer product may comprise C20+ olefins in an amount ranging from 30 wt. % to 90 wt. % (e.g., 35 wt. % to 80 wt. %, or 40 wt. % to 70 wt. %).

In some aspects, the oligomer product may comprise C10-C60 oligomers in an amount of at least 30 wt. % (e.g., at least 40 wt. %, or at least 50 wt. %). For example, the oligomer product may comprise C10-C60 oligomers in an amount ranging from 30 wt. % to 99 wt. % (e.g., 35 wt. % to 95 wt. %, or 40 wt. % to 90 wt. %).

In some aspects, the oligomer product may comprise at least 50 wt. % of C10-C40 oligomers having boiling points in the jet and diesel fuel range (e.g., 150° C. to 400° C.). For example, the oligomer product may comprise from 50 wt. % to 90 wt. % (e.g., 55 wt. % to 85 wt. %) of C10-C60 oligomers having boiling points in the jet and diesel fuel range.

In some aspects, the oligomer product may comprise at least 50 mol. % (e.g., at least 60 mol. %) of tri-substituted olefins and tetra-substituted olefins. For example, the oligomer product may comprise from 50 mol. % to 90 mol. % (e.g., 60 mol. % to 80 mol. %) of tri-substituted and tetra-substituted olefins.

The raw oligomer product may be fractionated (e.g., by distillation) into different fuel grades, each of which is known to be within a certain boiling point range. For example, fractionation may be conducted at a determined fractionation temperature or boiling point cut-off (e.g., 120° C. to 300° C. or 300° C. to 400° C.) to separate out various boiling point fractions appropriate to a desired fuel product and to collect olefinic light products for further processing. The light fraction (120° C.−) may be recycled to the oligomerization step for conversion to hydrocarbon fuels, thereby increasing yield to products in the distillate range. Distillate olefin fractions can be in any or all of the jet, diesel, or other fuel ranges. These fractions can be hydrogenated to provide paraffin and isoparaffin fuels or fuel blend stocks. Heavy olefin fractions (400° C.+) boiling above a desired fuel range can be cracked over selected catalysts to produce lower boiling fractions.

Fractionation may be conducted prior to hydrogenation to form light olefin distillates and olefin heavy products that can be further processed independently.

In some aspects, fractionation may be conducted upon completion of all other post-processing (e.g., hydrogenation) in order to more accurately control the composition of the collected fractions. Such control might be desirable, for example, if a specific boiling point range were desired to meet the specifications of a desired fuel type.

Hydrogenation

The oligomer product or fractions thereof may be hydrogenated to produce hydrogenated oligomer products which may be used as fuels and fuel blend stocks.

The hydrogenation may be carried out by any appropriate method known in the art. The hydrogenation is typically carried out in the presence of a hydrogenation catalyst and a hydrogen source.

The catalyst may be any suitable hydrogenation catalyst, such as a palladium catalyst supported on activated carbon or a Raney nickel catalyst.

The hydrogen source may include in situ generated $H_2$, external $H_2$, recycled $H_2$, or a combination thereof.

Any reactor known in the art being appropriate for performing the hydrogenation may be employed. In some aspects, a trickle bed reactor is employed for performing the hydrogenation.

The hydrogenation conditions may include an operating temperature in a range of from 100° C. to 400° C. (e.g., 150° C. to 350° C.).

The pressure may be in a range of from 100 psig to 2000 psig (689 kPa to 13.8 MPa), such as 500 psig to 1000 psig (3.4 MPa to 6.9 MPa).

Feed may be introduced to the hydrogenation reactor at a weight hourly space velocity (WHSV) in range of from 0.1 $h^{-1}$ to 50 $h^{-1}$ (e.g., 0.5 $h^{-1}$ to 10 $h^{-1}$).

A preferred aspect is the use of a complete saturation process as the hydrogenation process. Suitable catalysts will completely saturate mono- and polyolefinic hydrocarbons without significant cracking or polymerization activity. As such, the hydrogenated oligomer product stream can include less than 0.1 wt. % alkenes (e.g., less than 0.01 wt. % alkenes).

Hydrogenated oligomer products from the hydrogenation reactor may be collected or further fractionated to obtain a desired fuel, such as jet or diesel, or a fuel blend stock product.

EXAMPLES

The following illustrative examples are intended to be non-limiting.

Example 1-1 (Comparative)

A fixed-bed reactor was charged with 10 $cm^3$ of a commercial alumina catalyst. Anhydrous ethanol was continuously fed to the reactor by a Quizix pump. The internal reactor temperature was maintained at 620° F. and the reactor pressure was 100 psig. The LHSV of the ethanol was 1 $h^{-1}$. The gas product was collected and analyzed by gas chromatography (GC). The liquid product was collected and analyzed by high-performance liquid chromatography (HPLC). Under these conditions, the ethanol conversion was low (68.6%) with low ethylene selectivity (56.4%) and significant diethyl ether formation (39.3%). The results are reported in Table 1.

Example 1-2 (Comparative)

Example 1-1 was repeated except that internal reactor temperature was maintained at 700° F. and the LHSV was increased to 2.0 $h^{-1}$. Under these conditions, the ethanol conversion was increased to 92% and the diethyl ether content was reduced to 2.2 wt. %. The results are reported in Table 1.

Example 2-1 (Invention)

Example 1-1 was repeated except that internal reactor temperature was maintained at 700° F. and the LHSV was increased to 1.5 $h^{-1}$. Under these conditions, the ethanol conversion was increased to 95% and the diethyl ether content was reduced to 0.9%. The results are reported in Table 1.

Example 2-2

Example 1-1 was repeated except that internal reactor temperature was maintained at 700° F. and the LHSV was the same, 1.0 $h^{-1}$. Under these conditions, the ethanol conversion was high (98.9%) with high ethylene selectivity (92%). No diethyl ether was formed. The results are reported in Table 1.

Example 2-3

Example 1 was repeated except that internal reactor temperature was maintained at 700° F. and the LHSV was reduced to 0.5 $h^{-1}$. Under these conditions, the ethanol conversion was high (99.4%) with high ethylene selectivity (91.1%). No diethyl ether was formed. The results are reported in Table 1.

TABLE 1

Ethanol Dehydration

| | Ex. 1-1 | Ex. 1-2 | Ex. 2-1 | Ex. 2-2 | Ex. 2-3 |
|---|---|---|---|---|---|
| Process Conditions | | | | | |
| Temperature [° F.] | 620 | 700 | 700 | 700 | 700 |
| Pressure [psig] | 100 | 100 | 100 | 100 | 100 |
| LHSV [$h^{-1}$] | 1.0 | 2.0 | 1.5 | 1.0 | 0.5 |
| Ethylene Conversion [%] | 68.6 | 92 | 95 | 98.9 | 99.4 |
| Product Selectivity [%] | | | | | |
| Ethylene | 56.4 | 94.1 | 93.8 | 92.0 | 91.1 |
| Ethane | 0 | 0 | 0 | 0.2 | 0 |
| Propylene | 0 | 0.1 | 0.2 | 0.3 | 0.4 |
| Butenes | 4.3 | 3.5 | 5.0 | 7.0 | 7.8 |
| Pentenes | 0 | 0 | 0.1 | 0.3 | 0.5 |
| Diethyl Ether | 39.3 | 2.2 | 0.9 | 0 | 0 |

The data in Table 1 show that for ethanol dehydration, a very high conversion of ethanol (95% or higher) is required in order to achieve an oxygen content to less than 1 wt. %. By running at a high conversion, 95% or higher, recycling of the unconverted ethanol can be eliminated and undesirable oxygenate formation can be minimized that can damage the ionic liquid catalyst in the olefin oligomerization step.

Example 3 (Comparative)

A fixed-bed reactor was charged with 10 $cm^3$ of a commercial alumina catalyst. Anhydrous isobutanol was continuously fed to the reactor by a Quizix pump. The internal reactor temperature was maintained at 570° F. and the reactor pressure was 100 psig. The LHSV of the isobutanol was 1 $h^{-1}$. The gas product was collected and analyzed by GC. The liquid products were collected and analyzed by HPLC. Under these conditions, the isobutanol conversion was low (54.6%). The results are summarized in Table 2.

Example 4 (Invention)

Example 3 was repeated except that internal reactor temperature was maintained at 620° F. Under these conditions, the isobutanol conversion was high (99.5%). The results are summarized in Table 2.

TABLE 2

Dehydration of Isobutanol

| | Example 3 | Example 4 |
|---|---|---|
| Process Conditions | | |
| Temperature [° F.] | 570 | 620 |
| Pressure [psig] | 100 | 100 |
| LHSV [$h^{-1}$] | 1.0 | 1.0 |
| Isobutylene Conversion [%] | 54.6 | 99.5 |
| Product Selectivity [%] | | |
| Isobutylene | 95.3 | 91.6 |
| trans-2-Butene | 1.6 | 3.6 |
| cis-2-Butene | 2.5 | 4.8 |
| 1-Butene | 0.0 | 0.0 |

The data in Table 2 show that for butanol dehydration, it is much easier to achieve very high conversion of butanol. Dehydration produces generally pure C4 olefins. Again, it is desirable to run at a high conversion, 95% or higher. Then recycling of the unconverted butanol can be eliminated and undesirable oxygenate formation can be minimized that can damage the ionic liquid catalyst in the olefin oligomerization step.

Example 5

The ionic liquid catalyst used herein for oligomerization was 1-butylpyridinium chloroaluminate. The composition of the ionic liquid is set forth in Table 3. The density of the ionic liquid was 1.34 $g/cm^3$.

TABLE 3

Composition of the 1-Butylpyridinium Chloroaluminate Ionic Liquid Catalyst

| Element | Wt. % |
|---|---|
| Al | 12.4 |
| Cl | 56.5 |
| C | 24.6 |

TABLE 3-continued

Composition of the 1-Butylpyridinium
Chloroaluminate Ionic Liquid Catalyst

| Element | Wt. % |
|---------|-------|
| H | 3.2 |
| N | 3.3 |

Example 6 (Comparative)

Ethylene Oligomerization in Semi-Batch Mode

In a glove box, n-heptane (54 g) and 1-butylpyridinium chloroaluminate ionic liquid catalyst (72 g) were added to a 300-cm³ autoclave reactor. The reactor was removed from the glove box. The reactor was heated to 50° C. (122° F.) and the mixture was stirred at 1200 rpm. While stirring, chemical grade ethylene (>99.5% purity) was fed into the autoclave using a flow controller setting at 1000 cm³/min with a constant back pressure of 500 psig. Due to high vapor pressure of ethylene gas and very low conversion of ethylene, the reactor was filled with ethylene gas and reached to 500 psig rather rapidly, thus continuing steady addition of ethylene was difficult. For duration of 1 hour, only 35 g of ethylene (30 L of gas) was fed to the reactor. During the course of ethylene addition, the temperature was held at 50° C. (122° F.). After the 1-hour addition of ethylene gas, the autoclave was stirred at 1200 rpm for 30 minutes.

During the reaction, the autoclave reactor contained a multi-phasic mixture, a gaseous phase containing ethylene and HCl and two immiscible liquid phases: an ionic liquid phase and a hydrocarbon phase containing oligomerized products and n-heptane solvent. Inert n-heptane solvent was added to improve the contact between ethylene in the gas phase and the ionic liquid catalyst. Based on the final volume of reactor with an internal volume of 280 mL, the above addition conditions corresponded to 20 vol. % ionic liquid catalyst and 30 vol. % of n-heptane.

The autoclave was degassed to atmospheric pressure, and then the immiscible liquid phases were separated using a glass separatory funnel into an ionic liquid phase and a hydrocarbon phase containing oligomer products and n-heptane. The hydrocarbon phase was washed with deionized water to remove any entrained ionic liquid catalyst. The washed hydrocarbon product was dried with MgSO$_4$, and then the MgSO$_4$ was removed by vacuum filtration using 0.7 micron filter paper. The dried hydrocarbon phase was analyzed by simulated distillation (Simdist, ASTM D2887). The simulated distillation data was corrected to subtract the n-heptane solvent and then re-normalized to obtain the boiling point distribution of the oligomer products only. The oligomer yield was very low, less than 4.5 g of oligomer product was obtained. The results are summarized in Table 4.

Example 7-1

Ethylene Oligomerization in Semi-Batch Mode Using a Co-Catalyst

Example 6 was repeated except that anhydrous HCl gas (7.2 g) from a lecture bottle was added to the reactor and then the mixture was stirred at 1200 rpm. Then the autoclave was heated to 50° C. before the ethylene gas was added.

For this example, no issues of feeding ethylene gas were observed since ethylene gas reacted rapidly to form liquid oligomer product and created headroom in the reactor for fresh ethylene gas addition. While the back pressure regulator was set at 500 psig, the pressure was maintained less than 500 psig for the entire duration of the reaction, which indicated almost complete conversion of ethylene. A total of 74 g of ethylene (63 L of gas) was fed to the reactor during the 1-hour addition period. The molar ratio of olefin to HCl at the end of the reaction was 13. About 37 g of oligomerized olefin product was obtained. The results are summarized in Table 4.

Example 7-2

Ethylene Oligomerization in Continuous Mode

A continuous microunit with a 100 mL autoclave reactor was used to oligomerize ethylene. The reactor was initially charged with n-heptane. Then, 1-butylpyridinium chloroaluminate ionic liquid catalyst (0.2 g/min), anhydrous HCl gas (5.0 cm³/min) and chemical-grade ethylene gas (190 cm³/min) were added in a continuous manner while the reactor was maintained at a temperature of 122° F., an outlet pressure of 400 psig and an agitation rate of 1200 rpm. Assuming ethylene and HCl are dissolved into the liquid hydrocarbon phase in the reactor, these conditions correspond to 20 vol. % ionic liquid catalyst and a reaction residence time of 120 minutes. The ethylene to HCl molar ratio was 41.

The reactor effluent was de-pressurized to ambient pressure and separated continuously with a 3-phase separator into a gas phase, a hydrocarbon phase containing oligomer product and an ionic liquid phase.

The hydrocarbon phase was washed in batch with an equal volume of deionized water to remove any residual ionic liquid catalyst. The washed hydrocarbon oligomer product was dried with MgSO$_4$ and then the magnesium sulfate drying agent was removed by vacuum filtration using a 0.7 micron filter paper. The dried oligomer was analyzed by simulated distillation (Simdist, ASTM D2887).

The results are reported in Table 4. A 68% conversion of ethylene to oligomer product was achieved. The oligomer product had a jet+diesel product selectivity of 47%.

Example 7-3

Ethylene Oligomerization in Continuous Mode

Example 7-2 was repeated except that the amount of anhydrous HCl gas was increased to 9.3 cm³/min. The ethylene to HCl molar ratio was 22.

The results are reported in Table 4. A 77% conversion of ethylene to oligomer product was achieved. The oligomer product exhibited a high jet+diesel product selectivity of 69%.

TABLE 4

Ethylene Oligomerization with Ionic Liquid Catalyst

| | Ex. 6 | Ex. 7-1 | Ex. 7-2 | Ex. 7-3 |
|---|---|---|---|---|
| Process Mode | Semi-Batch | Semi-Batch | Continuous | Continuous |
| Process Conditions | | | | |
| Temperature [° F.] | 122 | 122 | 122 | 122 |
| Pressure [psig] | 500 | 470 | 400 | 400 |
| Ionic Liquid [vol. %] | 20 | 20 | 20 | 20 |
| Olefin/HCl molar ratio | — | 13 | 41 | 22 |
| Simdist [° F.] | | | | |
| Initial Boiling Point (IBP) | 215 | 212 | 172 | 175 |
| @ 10 wt. % | 322 | 258 | 409 | 337 |
| @ 30 wt. % | 481 | 345 | 575 | 458 |

TABLE 4-continued

Ethylene Oligomerization with Ionic Liquid Catalyst

|  | Ex. 6 | Ex. 7-1 | Ex. 7-2 | Ex. 7-3 |
|---|---|---|---|---|
| @ 50 wt. % | 625 | 420 | 713 | 570 |
| @ 70 wt. % | 751 | 516 | 840 | 693 |
| @ 90 wt. % | 867 | 671 | 964 | 873 |
| Final Boiling Point (FBP) | 944 | 888 | 1025 | 1016 |
| Oligomer Boiling Range Distribution [%] | | | | |
| 215° F.-250° F. | 9 | 7 | 1 | 2 |
| 250° F.-700° F. | 58 | 85 | 47 | 69 |
| 700° F.+ | 33 | 8 | 52 | 28 |
| Oligomer Yield[a] [%] | 12 | 50 | 68 | 77 |
| Jet + Diesel Selectivity[b] [%] | 58 | 85 | 47 | 69 |

[a]Oligomer Yield = [(weight of oligomer product/weight of ethylene feed)] × 100
[b]Jet + Diesel Product Selectivity = [(weight of product in 250° F.-700° F. boiling range/total oligomer product) ] × 100.

Example 8

The oligomer product from Example 7-3 was distilled in a laboratory into light distillate (kerosene and jet), heavy distillate (diesel) and lubricating oil fractions. The properties of these fractions are summarized in Table 5.

TABLE 5

Oligomer Properties from Ethylene Oligomerization

| Light Distillate (250° F.-500° F.) | |
|---|---|
| Flash Point [° F.] | 111.2 |
| Freeze Point [° F.] | <−76 |
| Cloud Point [° F.] | <−76 |
| Cetane Index | 48.2 |
| Specific Gravity | 0.7622 |
| Sulfur [ppm ] | <5 |
| Heavy Distillate (500° F.-700° F.) | |
| Flash Point [° F.] | 273.2 |
| Freeze Point [° F.] | <−76 |
| Cloud Point [° F.] | <−76 |
| Cetane Index | 56.8 |
| Specific Gravity | 0.8084 |
| Sulfur [ppm] | <5 |
| Heavy Portion (700° F.+) | |
| Pour Point [° F.] | −5.8 |
| Cloud Point [° F.] | <−76 |
| KV40 [mm$^2$/s] | 558.0 |
| KV100 [mm$^2$/s] | 24.8 |
| Viscosity Index | 41 |

Flash point was according to ASTM D93. Freeze point was determined according to ASTM D2386. Cloud point was determined according to ASTM D2500. Cetane index was determined according to ASTM D4737. Specific gravity at 15.6° C. can be determined according to ASTM D4052. Sulfur content was determined according to ASTM D2622. Pour point was determined according to ASTM D97. Kinematic viscosity was determined according to ASTM D445. Kinematic viscosity at 100° C. is reported herein as KV100, and kinematic viscosity at 40° C. is reported herein as KV40.

The product properties in Table 5 indicate that the process makes very high quality distillate with excellent freeze and cloud points indicating these streams can be used to improve the characteristics of jet or diesel blends. Additionally, the distillate fractions exhibited very good cetane index and low sulfur content.

The above olefin products can be sent to hydrogenation unit to saturate the olefins before blending into the various hydrocarbon products.

Example 9 (Comparative)

Non-Optimized Propylene Oligomerization in Semi-Batch Mode

Pure chemical grade propylene gas was used for this example where propylene gas was oligomerized to produce an oligomer product via semi-batch process.

In a glove box, 54 g of n-heptane, 15 g of ionic liquid catalyst and 0.6 g of tert-butyl chloride were charged to a 300-cm$^3$ autoclave reactor. Then the autoclave was taken out of the glove box and the mixture was stirred at 1200 rpm. While stirring, propylene (C3=) gas (~150 psig of supply pressure) was fed into the autoclave using a flow controller at 870 cm$^3$/min for 60 minutes, total 98 g of propylene was added. During the course of propylene addition, the temperature was controlled with an internal cooling coil at around 84° F. At the end of the propylene addition, the reactor pressure was 57 psig. The low reactor pressure compared to the propylene gas supply pressure during the reaction indicates that the propylene gas reacted rapidly during the addition and converted into a liquid oligomer product.

Based on the internal reactor volume of 280 cm$^3$, the heptane and ionic liquid catalyst volumes of the described above correspond to 4 vol. % ionic liquid catalyst, 30 vol. % of heptane. The final mole ratio of propylene to tert-butyl chloride was 350. After the addition of propylene gas, the autoclave was continued to stir for 30 more minutes at 1200 rpm. A summary of the process conditions is reported in Table 6.

After the reaction, the autoclave reactor was opened and the reaction product was separated using a glass separatory funnel into a hydrocarbon phase containing n-heptane and an oligomer product, and an ionic liquid catalyst phase. The hydrocarbon phase was washed with deionized water to remove the residual ionic liquid catalyst. The washed hydrocarbon product was dried with magnesium sulfate powder drying agent, and then the magnesium sulfate drying agent was removed by vacuum filtration using a 0.7 micron filter paper.

The dried hydrocarbon phase was analyzed by high-temperature simulated distillation test (ASTM D6417). The simulated distillation data was corrected to subtract the heptane solvent and then re-normalized to obtain the boiling point distribution of the oligomer product only. The distillation results are reported in Table 6 and FIG. 2.

The yield of C9-C40 carbon range oligomer was estimated using the weight percent data corresponding to 250° F.-1000° F. of the simulated distillation.

Example 10-1 (Invention)

Improved Propylene Oligomerization in Semi-Batch Mode

Figure 2:
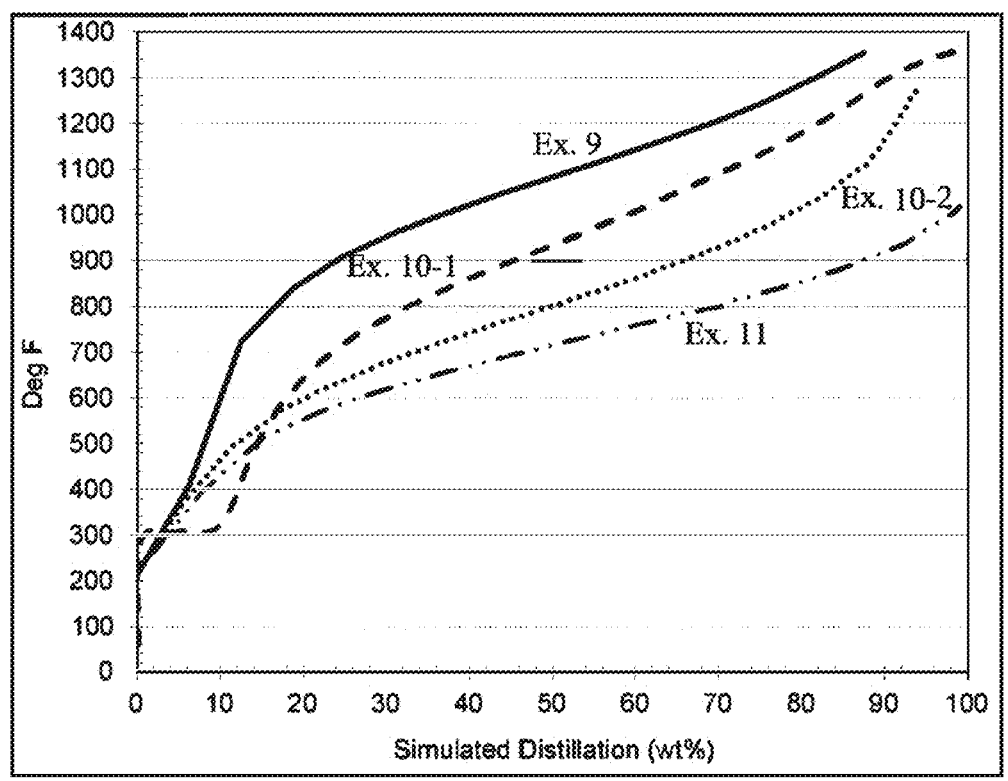
FIG. 2 shows a boiling point distribution of oligomer products from propylene.

The same equipment, reagents and procedure as in Example 9 were used for this example except the reaction temperature. The autoclave reactor was taken out of the glove box, and the mixture was stirred at 1200 rpm and heated to 122° F. before the propylene gas was added. The process conditions and product boiling point distribution are reported in Table 6. Simulated distillation plot of the oligomer product is shown in FIG. 2.

Example 10-2 (Invention)

Optimized Propylene Oligomerization in Semi-Batch Mode

The same equipment, reagents and procedure as in Example 9 were used for this example except the reaction temperature and the amount of tert-butyl chloride usage. In a glove box, 54 g of n-heptane, 15 g of ionic liquid catalyst and 1.5 g of tert-butyl chloride were added to a 300-cm$^3$ autoclave reactor. Then the autoclave was taken out of the glove box, and the mixture was stirred at 1200 rpm and heated to 176° F. before the propylene gas was added. The process conditions and product boiling point distribution are reported in Table 6. Simulated distillation plot of the oligomer product is shown in FIG. 2.

TABLE 6

Propylene Oligomerization with Ionic Liquid Catalyst

|  | Example 9 Comparative | Ex. 10-1 Invention | Ex. 10-2 Invention |
|---|---|---|---|
| Process Conditions |  |  |  |
| Olefin source | C3= | C3= | C3= |
| Temperature [° F.] | 84 | 122 | 176 |
| Final Pressure [psig] | 57 | 11 | — |
| Ionic Liquid Catalyst [vol. %] | 4 | 4 | 4 |
| t-BuCl [vol. %] | 0.16 | 0.16 | 0.4 |
| Olefin/t-BuCl molar ratio | 350 | 350 | 140 |
| Simdist [° F.] |  |  |  |
| IBP | 213 | 289 | 215 |
| @ 10 wt. % | 654 | 324 | 422 |
| @ 30 wt. % | 963 | 776 | 687 |
| @ 50 wt. % | 1082 | 935 | 832 |
| @ 70 wt. % | 1219 | 1091 | 926 |
| @ 90 wt. % | 1393 | 1299 | 1136 |
| FBP | >1393 (90%) | 1365 (99.5%) | >1277 (94%) |
| Olefin Conversion$^{(a)}$ [wt. %] | 100 | 100 | 100 |
| Oligomer Product Selectivity$^{(b)}$ |  |  |  |
| C9− Oligomer Yield [wt. %] (215-250° F.) | 1 | 0 | 4 |
| C9-C40 Oligomer Yield [wt. %] (250-1000° F.) | 37 | 59 | 75 |
| C40+ Oligomer Yield [wt. %] (1000-1500° F.) | 62 | 41 | 21 |

$^{(a)}$wt. % Oligomer Conversion = [(weight of olefin in feed − weight of olefin in gas product)/(weight of olefin in feed)] × 100
$^{(b)}$Oligomer Product Selectivity = [(weight of product in a selected boiling range)/(total oligomer product)] × 100

The boiling point distribution curves of Examples 9, 10-1 and 10-2 shown in FIG. 2 and the corresponding data summarized in Table 6 clearly show the advantage of the present invention. In comparison to Example 9, Examples 10-1 and 10-2 increased the yield of C9-C40 carbon range oligomer substantially by adjusting the process conditions.

When the tert-butyl chloride promoter amount was not adequate and the reaction temperature was low (Example 9), the oligomer product was very heavy with a high final boiling point is around 1400° F. The oligomer product showed only 37% of C9-C40 carbon range oligomer product selectivity.

When the reactor temperature was raised to 122° F. (Example 10-1), the final boiling point of the oligomer product was lowered to 1365° F. and the product selectivity for the C9-C40 carbon range oligomer product was improved to 59%.

Another important variable affecting the product carbon number distribution is the amount of tert-butyl chloride promoter used. When the amount of tert-butyl chloride was increased to 0.4 vol. % and the reactor temperature was raised to 176° F. (Example 10-2), a significant improvement of boiling point distribution was observed. The oligomer product showed much improved selectivity of C9-C40 carbon range oligomer to 75 wt. %, and the final boiling point was lowered to about <1300° F.

Without being bound by any theory, Brønsted acidity is added to the Lewis acidity of AlCl$_3$ in the ionic liquid catalyst by adding the varying amount of tert-butyl chloride promoter additive. The halide-containing organic additive is converted to hydrogen halide (i.e., HCl in Examples 9, 10-1 and 10-2) upon contact with the ionic liquid catalyst. The Brønsted acidity appears to control the termination of oligomerization process, wherein a higher dose of Brønsted acidity induces downward shifts of the molecular weight, the carbon number distribution and the boiling point distribution in the oligomer product. The tert-butyl chloride could also form a tertiary carbocation, which could act as an oligomerization promoter/initiator. Possibly the higher concentration of promoter/initiator gives smaller chains because there is an increase in concentration of chain-growing oligomers, so more chains at lower molecular weights compared to fewer chains at higher molecular weights. Higher reaction temperature also has a similar effect, but the extent is somewhat less.

The desirable oligomer yield can be further improved by using a continuous mode of stirred tank reactor (CSTR) operation. Example 11 shows oligomerization of propylene gas in a continuous mode operation.

Example 11 (Invention)

Further Optimized Propylene Oligomerization in Continuous Mode

A continuous microunit with 100 cm$^3$ autoclave reactor was used to oligomerize pure chemical grade propylene gas to produce an oligomer product in a continuous manner.

A mixture solution of tert-butyl chloride and n-heptane was created by mixing 6.6 g of tert-butyl chloride per 1000 g of heptane. To a 100-cm$^3$ reactor, 1.37 g/min of the n-heptane/tert-butyl chloride mixture solution, 0.09 g/min of the ionic liquid catalyst from Example 5, and 1290 cm$^3$/min propylene gas were added in a continuous manner while the reactor was maintained at a temperature of 248° F., an outlet pressure of 50 psig and an agitation rate of 1200 rpm. These conditions correspond to 1 vol. % ionic liquid catalyst, 0.1 vol. % tert-butyl chloride promoter, 30 vol. % n-heptane solvent and the remainder volume (~69%) of propylene oligomer/liquid propylene in the reactor and a reaction residence time of 15 minutes.

The reactor effluent was separated continuously with a 3-phase separator into a gas phase, a hydrocarbon phase containing n-heptane and oligomer product and an ionic liquid phase. Propylene was nearly completely converted and the gas-make was close to zero.

The hydrocarbon phase was washed in batch with an equal volume of deionized water to remove the residual ionic liquid catalyst. The washed hydrocarbon product was dried with magnesium sulfate powder drying agent, and then the magnesium sulfate drying agent was removed by vacuum filtration using a 0.7 micron filter paper. The dried hydrocarbon phase was analyzed by simulated distillation (ASTM D2887).

The process conditions and product boiling point distribution are reported in Table 7. Simulated distillation plot of the oligomer product is shown in FIG. 2.

TABLE 7

Effects of Olefin Feeds on Oligomer Product with Ionic Liquid Catalyst

|  | Ex. 11 Invention | Ex. 12 Invention | Ex. 13 Invention | Ex. 14 Invention |
|---|---|---|---|---|
| Process Conditions | Continuous | Continuous | Continuous | Batch |
| Olefin source | C3= | C3=/C4= | Mixed C4= | C5= |
| Presence of isoparaffin | No | Yes | Yes | No |
| Iso/olefin molar ratio[a] | 0 | 0.89 | 0.75 | 0 |
| Temperature [° F.] | 248 | 248 | 248 | 248 |
| Pressure [psig] | 50 | 100 | 100 | — |
| Ionic Liquid [vol. %] | 1 | 3 | 5 | 3 |
| t-BuCl [vol. %] | 0.1 | 0.15 | 0.3 | 0.15 |
| Olefin/t-BuCl molar ratio | 590 | 100 | 100 | 200 |
| Simdist [° F.] | | | | |
| IBP | 215 | 214 | 213 | 216 |
| @ 10 wt. % | 511 | 382 | 250 | 264 |
| @ 30 wt. % | 607 | 485 | 396 | 312 |
| @ 50 wt. % | 756 | 576 | 516 | 353 |
| @ 70 wt. % | 808 | 670 | 620 | 433 |
| @ 90 wt. % | 913 | 818 | 751 | 571 |
| FBP | 1019 | 998 | 952 | 820 |
| Olefin Conversion[b] [wt. %] | 99 | ~99 | ~99 | ~99 |
| Oligomer Product Selectivity[c] | | | | |
| C9- Oligomer [wt. %] (215-250° F.) | 5 | 6 | 10 | 7 |
| C9-C40 Oligomer [wt. %] (250-1000° F.) | 93 | 94 | 90 | 93 |
| C40+ Oligomer [wt. %] (1000-1500° F.) | 2 | 0 | 0 | 0 |

[a]Isoparaffin to olefin molar ratio
[b]wt % Oligomer Conversion = [(weight of olefin in feed − weight of olefin in gas product)/(weight of olefin in feed) ] × 100
[c]Oligomer Product selectivity = [(weight of product in a selected boiling range)/(total oligomer product) ] × 100

With a continuous process unit operation, a 99% conversion of propylene to oligomer product was achieved. The oligomer product shows further improvement of C9-C40 carbon range oligomer product selectivity of 93 wt. %. The simulated distillation curve shown in FIG. 2 clearly demonstrates the significant shifting in boiling point distribution to the desirable direction.

The propylene oligomerization results from Examples 9, 10-1, 10-2 and 11 show that the propylene oligomerization process can be further optimized in a continuous process by controlling the Brønsted acidity of the catalyst, the catalyst amount (total amount of active sites), and the reaction temperature.

The amount of tert-butyl chloride needed for the continuous process is much less than that of the semi-batch process. It was likely due to more efficient use of tert-butyl chloride in the continuous mode by minimizing the formation of undesirable, chlorinated conjunct polymers that would deactivate the ionic liquid catalyst.

It was also discovered the oligomerization process can be applied to a wide range of olefin feeds. Example 12 shows oligomerization of liquid-phase propylene/butene mixture in a continuous mode reaction. Example 13 shows oligomerization of liquid-phase butene mixture in a continuous mode reaction. Example 14 shows liquid-phase pentene oligomerization in a batch mode.

Example 12 (Invention)

C3=/C4=Mixed Olefin Feed Oligomerization in Continuous Mode

A refinery olefin stream containing C3 and C4 olefins from a Fluid Catalytic Cracking Unit (FCC unit) with the composition shown in Table 8 was used for this example. The feed contained about 20 ppm of sulfur.

TABLE 8

Refinery Stream Composition

| Component | Wt. % |
|---|---|
| Propane (C3) | 5 |
| Propene (C3=) | 10 |
| Isobutane (iC4) | 40 |
| n-Butane (nC4) | 15 |
| 1-Butene (1-C4=) | 7 |
| 2-Methylpropene (iC4=) | 8 |
| trans-2-Butene (t-2-C4=) | 9 |
| cis-2-Butene (c-2-C4=) | 6 |
| Isopentane (iC5) | 0.1 |
| Mixed Pentene (C5=) | 0.1 |

The refinery feed was oligomerized in a microunit with 3 vol. % ionic liquid catalyst, 10 vol. % n-heptane solvent and olefin/t-BuCl molar ratio of 100 at 248° F., 100 psig and 1200 rpm agitation.

Propane and n-butane in the feed as well as n-heptane solvent are completely inert and do not participate in the oligomerization process. However, isoparaffins, such as isobutane and isopentane, could alkylate the olefinic oligomer and convert it to saturated molecules. The molar ratio of isoparaffin to olefin of the above feed was 0.89.

The process conditions and product boiling point distribution are reported in Table 7. The distillation results show that the oligomer product from the C3=/C4=mixed feed shows excellent conversion and the C9-C40 carbon range oligomer product selectivity of 94%.

Example 12 (Invention)

Mixed C4=Refinery Feed Oligomerization in Continuous Mode

A refinery olefin stream containing mixed C4 olefin isomers from an FCC unit shown in Table 9 was used for this example. The feed contained about 60 ppm of sulfur.

TABLE 9

Refinery Stream Composition

| Component | Wt. % |
|---|---|
| Propane (C3) | 1 |
| Propene (C3=) | <1 |
| Isobutane (iC4) | 37 |
| n-Butane (nC4) | 10 |
| 1-Butene (1-C4=) | 10 |
| 2-Methylpropene (iC4=) | 15 |
| trans-2-Butene (t-2-C4=) | 15 |
| cis-2-Butene (c-2-C4=) | 10 |
| Isopentane (iC5) | 2 |
| Mixed Pentene (C5=) | <1 |

The refinery feed was oligomerized in a microunit with 5 vol. % ionic liquid catalyst, 10 vol. % n-heptane solvent and olefin/t-BuCl molar ratio of 100 at 248° F., 100 psig and 1200 rpm agitation.

Propane and n-butane in the feed as well as n-heptane solvent are completely inert and do not participate in the oligomerization process. However, isoparaffins, such as isobutane and isopentane, could alkylate the olefinic oligomer and convert it to saturated molecules. The molar ratio of isoparaffin to olefin of the above feed was 0.75.

The process conditions and product boiling point distribution are reported in Table 7. The distillation results show that the oligomer product from the mixed C4=feed shows excellent conversion and the C9-C40 carbon range oligomer product selectivity of 90 wt. %.

Example 13 (Invention)

C5=Feed Oligomerization in Batch Mode

Oligomerization of pure C5=(2-methyl-2-butene) was conducted in a batch autoclave reactor with 3 vol. % ionic liquid, 50 vol. % n-heptane solvent, olefin/t-BuCl (molar) ratio of 200, 248° F. reaction temperature and 1200 rpm agitation.

90 g of 2-methyl-2-butene, 90 g of n-heptane and 0.6 g of tert-butyl chloride were added to a 300-cm$^3$ autoclave reactor. The mixture was stirred at 1200 rpm and heated to 248° F. When the batch reactor temperature was stabilized at 248° F., 11 g of ionic liquid was added to the autoclave reactor for oligomerization reaction, and then continued the stirring for 1 hour.

After the reaction, the autoclave was opened and the reaction product was separated using a glass separatory funnel into a hydrocarbon phase containing n-heptane and an oligomer product, and an ionic liquid catalyst phase, as in Example 5. The hydrocarbon phase was washed with deionized water to remove the residual ionic liquid catalyst. The washed hydrocarbon product was dried with magnesium sulfate powder drying agent, and then the drying agent was removed by vacuum filtration using a 0.7 micron filter paper. The dried hydrocarbon phase was analyzed by simulated distillation test (ASTM D2887).

The process conditions and product boiling point distribution are reported in Table 7. The distillation results show that the oligomer product from the C5=feed shows excellent conversion and the C9-C40 carbon range oligomer product selectivity of 93%.

Inventive Examples 10-1, 10-2, 11, 12 and 13 reveal that the oligomerization process can be optimized by controlling the Brønsted acidity of the catalyst, the amount of organic chloride promoter, the ionic liquid catalyst amount (total amount of active sites), the reaction temperature and use of a continuous process. While the optimum conditions would vary depending on the feeds, a combination of the above variables would produce oligomer product for high selectivity for C9-C40 carbon range oligomer product.

Example 14

FIMS Analysis of Oligomer Product for Molecular Weight Determination

A Waters GCT Field Ionization Mass Spectrometer (FIMS) with FD/FI source analysis was used to determine the molecular weight distribution of the oligomer product. FIMS analysis is a soft ionization technique that typically does not fragment molecular ions. The analysis assumes a similar ionization response for all olefins. The injector temperature was 320° C. and the helium carrier gas flow rate at 1 mL/min.

Figure 3:
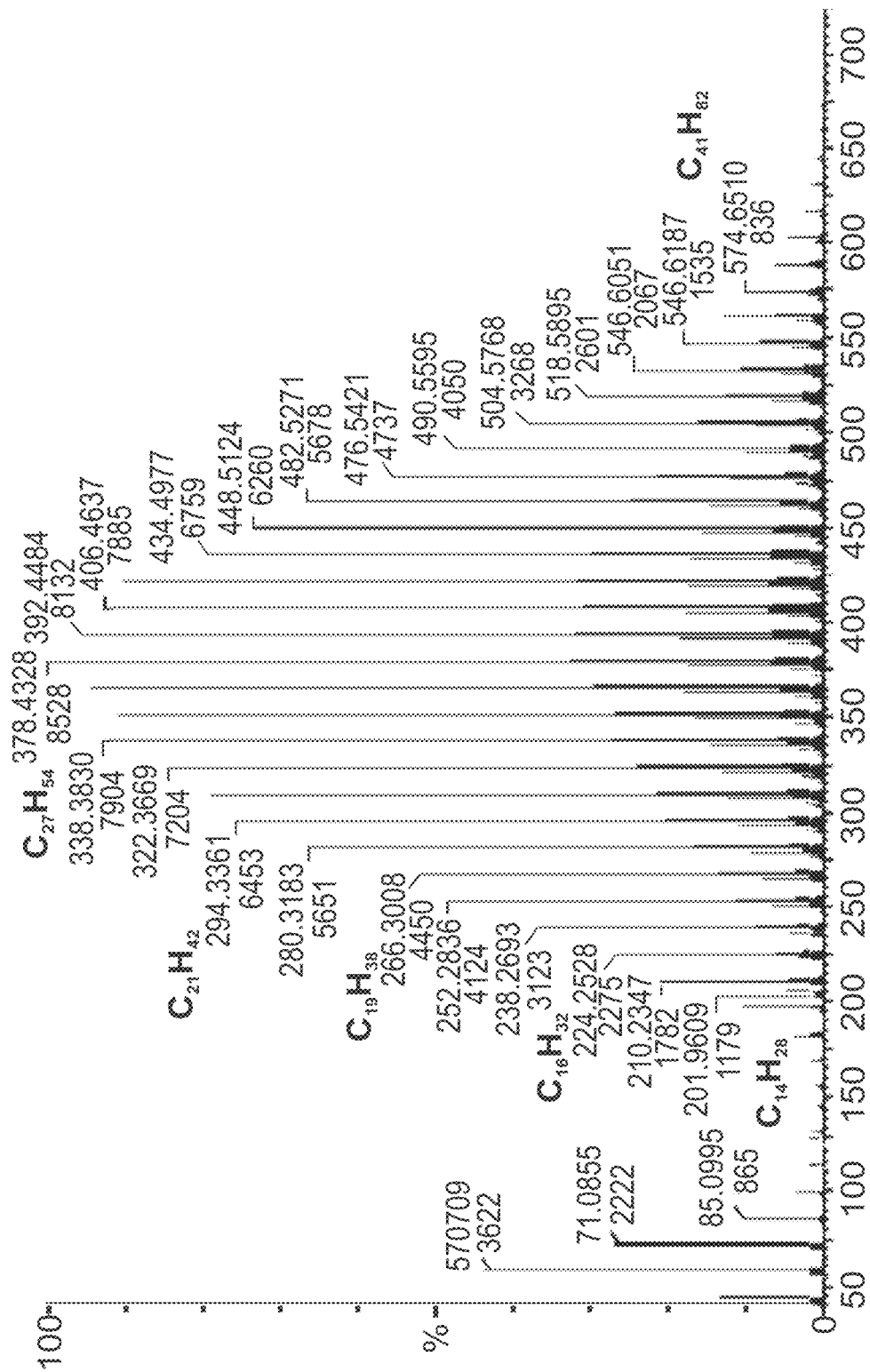
FIG. 3 shows a Field Ionization Mass Spectometry (FIMS) spectrum of a propylene olefin oligomer product.

FIG. 3 shows a FIMS spectrum of an oligomer product made from C3 olefin (Example 11). The average carbon number is defined as the molecular ion with 100% relative intensity typically at the center of the distribution range. The range of carbon number is from the lowest carbon number with at least 2% relative intensity to the highest carbon number with at least 2% relative intensity.

FIMS data shown FIG. 3 indicate that the oligomer product made from propylene (Example 11) is a mixture of mono-olefins that has the average carbon number of 27 and the carbon number distribution ranging from C14 to C43. There is a very small amount of light olefin fragments in the C4 to C10 range, which was created by fragmentation of molecules by FIMS instrument.

Another interesting feature in FIG. 3 is the Gaussian type uniform distribution of carbon numbers. Since the oligomer is made from propylene, it was expected that the relative intensities will be higher for the carbon numbers at the multiple of 3 (i.e., m/z=42 corresponding to —C$_3$H$_6$—) and the profile would show high and low relative intensity variations with the carbon number. Surprisingly, the oligomer carbon number was gradually increased by a unit of —CH$_2$— (m/z=14) and showed a uniform distribution. Even with C4 and C5 olefins, only gradual distribution of carbon numbers and no noticeable fluctuation of the relative intensities of carbon numbers relating to the feed olefin source were observed (data not shown).

For the effects the starting olefin feed source and the process conditions on carbon number distribution and other properties are summarized in Table 10.

TABLE 10

Properties of Oligomer Products from Various Olefin Sources

| | Ex. 11 | Ex. 12 | Ex. 13 | Ex. 14 |
|---|---|---|---|---|
| Olefin Feed | C3= | C3=/C4= | C4= | C5= |
| Presence of Isoparaffin | No | Yes | Yes | No |
| Iso/olefin molar ratio [a] | 0 | 0.89 | 0.75 | 0 |
| FIMS Analysis of Oligomer | | | | |
| Mono-Olefin Content | Nearly 100% | Nearly 100% | Nearly 100% | Nearly 100% |
| Carbon Number Range | 14-43 | 9-49 | 10-47 | 11-37 |
| Average Carbon Number | 27 | 26 | 24 | 20 |

TABLE 10-continued

Properties of Oligomer Products from Various Olefin Sources

|  | Ex. 11 | Ex. 12 | Ex. 13 | Ex. 14 |
|---|---|---|---|---|
| Olefin Type by $^1$H NMR [mol. %] | | | | |
| Di-substituted Olefin | 6 | 7 | 6 | 5 |
| Tri-substituted Olefin | 52 | 40 | 39 | 50 |
| Tetra-substituted Olefin | 34 | 48 | 49 | 39 |
| Alpha (vinyl) olefin | <1 | <1 | <1 | <1 |
| Vinylidene olefin | 8 | 4 | 5 | 6 |
| Branching Index | 57.9 | 65.7 | 67.7 | 66.0 |
| Bromine Number [g Br/100 g] | 26 | 48 | — | 67 |

Surprisingly, the carbon number distribution of oligomers made from different olefins, shown in Table 10, varied only slightly depending on the feed olefin and all oligomer products have the carbon numbers in the range of C9-C49.

Without being bound by theory, the FIMS results suggest that the ionic liquid catalyst/Brønsted acid system is very effective in disproportionating the carbon backbones and redistributes the carbon number of the oligomerized olefins. This rearrangement causes the shifting of carbon number redistribution to the Gaussian shape which in turn may affect the nature of the olefin species formed in the oligomer.

Another unique feature of the present process is that the product is a purely olefinic oligomer. The presence of isoparaffins in Examples 11 and 12 did not create paraffinic oligomer (i.e., saturated product) indicating that alkylation reaction is completely suppressed at process conditions. Likely use of tert-butyl chloride in a moderate amount made the ionic liquid catalyst in the acidity range that would suppress the alkylation reaction and little isoparaffin species, if any, are incorporated in the oligomer product.

Example 15

Determination of Olefin Type by NMR Analysis of Oligomerized Olefins

The oligomer products were characterized by proton nuclear magnetic resonance ($^1$H NMR) spectroscopy (400 MHz). The $^1$H NMR experimental parameters and analysis of the spectrum were performed according to the procedure described in US Patent Appl. Pub. No. 2008/0171672 to determine the olefin type (e.g., di-substituted, tri-substituted, tetra-substituted, alpha, or vinylidene olefin) in mol. %.

Figure 4:
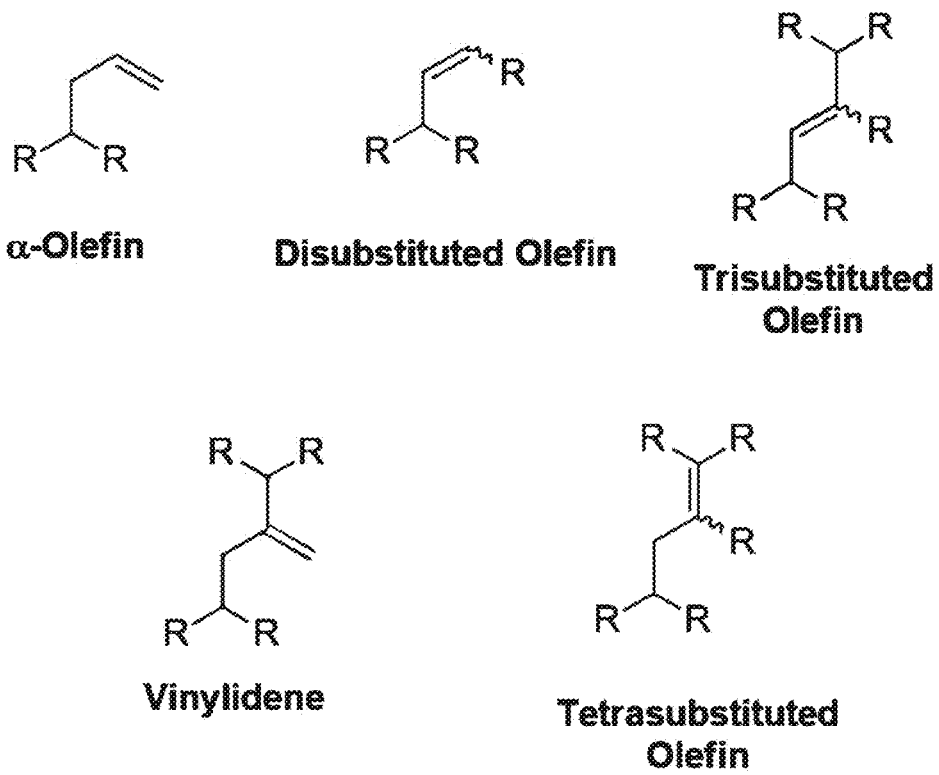
FIG. 4 shows potential olefin types present in oligomer products.

The general structures of the olefin types are shown in FIG. 4.

The amount of each olefin type in an olefin oligomer is expected vary depending on the starting olefin feed and the process conditions. The quantitation results for various olefin types are summarized in Table 10. Surprisingly, the olefin types of oligomers made from different olefins, shown in Table 10, varied only slightly depending on the feed olefin and all oligomer products have similar olefin type distribution.

The analysis reported in Table 10 indicates that the present process makes oligomer products with very high amounts of tri-substituted olefins (39-52 mol. %) and tetra-substituted olefins (34-49 mol. %). The amount of di-substituted olefins is in the range of 5-7 mol. % and vinylidene olefins in the range of 4-8 mol. %. In most cases, the alpha olefins represented less than 1 mol. % of all olefin types. The composition of oligomer with high contents of tri-substituted and tetra-substituted olefins was unexpected and has not been reported elsewhere.

Example 16

Method of Determining Branching Index with NMR $^1$H NMR spectroscopy was used to measure the branching index (BI). BI is defined as the % ratio of integral values of the methyl group (CH$_3$) protons compared to the sum of the methylene (CH$_2$) and methyl group protons (Equation 1). Allylic (H—CR$_2$—CR=CR$_2$) and methinyl protons (H—CR$_3$) are not considered in this analysis. $^1$H NMR spectra was recorded at 400 MHz on a Bruker instrument and chemical shifts are reported in ppm on a $\delta$ scale referenced to residual solvent (CHCl$_3$ in CDCl$_3$: 7.27 ppm). The integral of the methyl groups is defined as the peak area from $\delta$=0.20-1.01 ppm, and integral of the methylene groups are defined as the peak area from $\delta$=1.01-1.51.

Equation 1, Branching index (BI):

$$BI = \left( \int CH_3 / \int CH_3 + \int CH_2 \right) \times 100$$

The Branching Index of the oligomer olefin made from various olefin feeds via ionic liquid catalyst (Examples 11 through 14) was in the range of 58-68, reported in Table 10. The high Branching Index suggests that the oligomer olefin made from light olefins are highly branched.

The invention claimed is:
1. A renewable jet fuel prepared by:
   (a) dehydrating bio-based alcohols, with the bio-based alcohols comprising isobutanol, to form an olefin stream and a water stream wherein the dehydration process is conducted at selected process conditions sufficient to achieve conversion of the bio-based alcohols that is 95% or more and wherein an amount of oxygenates in the olefin stream is less than 1 wt %;
   (b) separating the olefin stream from the water stream;
   (c) contacting the olefin stream with a halometallate ionic liquid catalyst, the halometallate ionic liquid catalyst comprising an organic cation and a halometallate anion, in an oligomerization reactor under oligomerization conditions to form a mixture comprising the halometallate ionic liquid catalyst and an oligomer product, wherein the oligomer product comprises about 39-52 mol % tri-substituted olefins and 34-49 mol % tetra-substituted olefins, and with at least 50 wt % of the oligomer product having a boiling point distribution of from 150 C to 400 C;
   (d) separating the oligomer product from the halometallate ionic liquid catalyst; and
   (e) fractionating the oligomer product into various fractions and recovering a jet fuel fraction stream, which comprises from 50 to 90 mol % of tri-substituted and tetra-substituted olefins and has a branching index in the range of 56-68.
2. The renewable jet fuel of claim 1, wherein the jet fuel fraction stream recovered in (e) is hydrogenated.
3. The renewable jet fuel of claim 2, wherein the hydrogenated jet fuel fraction stream is prepared as a jet fuel which meets or exceeds the requirements of ASTM D1655-21.

4. The renewable jet fuel of claim 1, wherein the oligomer product in (d) is first hydrogenated and then fractioned in (e), with a jet fuel fraction stream recovered.

5. The renewable jet fuel of claim 4, wherein the recovered jet fuel fraction stream in (e) is prepared as a jet fuel which meets or exceeds the requirements of ASTM D1655-21.

6. The renewable jet fuel of claim 1, wherein the jet fuel comprises from 60 to 80 mol % of tri-substituted and tetra-substituted olefins.

* * * * *